(12) United States Patent
Kim et al.

(10) Patent No.: US 10,549,030 B2
(45) Date of Patent: Feb. 4, 2020

(54) LIQUID MEDICINE INJECTION DEVICE

(71) Applicant: EOFlow Co., Ltd., Seongnam-si (KR)

(72) Inventors: Seung Ha Kim, Goyang-si (KR); Jae Hong Kim, Namyangju-si (KR); Jesse Jaejin Kim, Seongnam-si (KR); Yongchul Song, Seongnam-si (KR); Jongook Jeong, Seongnam-si (KR)

(73) Assignee: EOFlow Co., Ltd., Seongnam-si (KR)

( * ) Notice: Subject to any disclaimer, the term of this patent is extended or adjusted under 35 U.S.C. 154(b) by 0 days.

(21) Appl. No.: 16/326,756

(22) PCT Filed: Aug. 1, 2017

(86) PCT No.: PCT/KR2017/008290
§ 371 (c)(1),
(2) Date: Feb. 20, 2019

(87) PCT Pub. No.: WO2018/048100
PCT Pub. Date: Mar. 15, 2018

(65) Prior Publication Data
US 2019/0192765 A1    Jun. 27, 2019

(30) Foreign Application Priority Data
Sep. 8, 2016 (KR) .................. 10-2016-0115650

(51) Int. Cl.
*A61M 5/142* (2006.01)
*A61M 5/145* (2006.01)
(Continued)

(52) U.S. Cl.
CPC ........ *A61M 5/14244* (2013.01); *A61M 5/145* (2013.01); *A61M 5/1723* (2013.01);
(Continued)

(58) Field of Classification Search
CPC .......... A61M 5/14248; A61M 5/14244; A61M 5/145; A61M 5/142; A61M 5/14;
(Continued)

(56) References Cited

U.S. PATENT DOCUMENTS 3,692,027 A * 9/1972 Ellinwood, Jr. .. A61M 5/14276
604/891.1
3,760,984 A * 9/1973 Theeuwes ............ A61K 9/0004
222/95
(Continued)

FOREIGN PATENT DOCUMENTS

EP    3037117    6/2016
JP    2000-265945    9/2000
(Continued)

OTHER PUBLICATIONS

Office Action dated Apr. 25, 2018 in Korean Patent Application No. 10-2016-0115650; 9 pages.

*Primary Examiner* — Nathan R Price
*Assistant Examiner* — Mark Alan Igel
(74) *Attorney, Agent, or Firm* — Knobbe, Martens, Olson & Bear LLP

(57) ABSTRACT

The present invention discloses a liquid medicine injection device that is attached to a patient's body to inject liquid medicine such as insulin at an appropriate time.
A liquid medicine injection device according to the present invention includes: a case; a liquid medicine tank that is disposed in the case and where liquid medicine is received; an electro-osmosis pump that is connected with the liquid medicine tank and moves the liquid medicine; a needle assembly that receives the liquid medicine by being connected to the electro-osmosis pump and injects the received liquid medicine into a human body; and an adhesive member combined to the case and attached to the human body.

6 Claims, 15 Drawing Sheets

(51) Int. Cl.
*A61M 39/24* (2006.01)
*A61M 5/172* (2006.01)
*A61M 5/168* (2006.01)
*A61M 31/00* (2006.01)

(52) U.S. Cl.
CPC ........... *A61M 39/24* (2013.01); *A61M 5/1684* (2013.01); *A61M 31/00* (2013.01); *A61M 2005/14252* (2013.01); *A61M 2230/201* (2013.01)

(58) Field of Classification Search
CPC .... A61M 5/00; A61M 5/14212; A61M 5/141; A61M 5/168; A61M 5/16804; A61M 5/16813; A61M 5/172; A61M 5/14224; A61M 39/24; A61M 2005/14513; A61M 2005/206; A61M 2005/2073; A61M 2005/2488; A61M 2005/2496; A61M 2005/3022; A61M 31/00; B01D 61/56; A61K 9/0004
USPC ...................................... 604/891.1
See application file for complete search history.

(56) References Cited

U.S. PATENT DOCUMENTS

| | | | | |
|---|---|---|---|---|
| 3,894,538 | A * | 7/1975 | Richter | A61M 5/14276 604/891.1 |
| 3,923,426 | A * | 12/1975 | Theeuwes | B01D 61/56 204/630 |
| 4,140,122 | A * | 2/1979 | Kuhl | A61M 5/14276 424/423 |
| 4,552,561 | A * | 11/1985 | Eckenhoff | A61M 5/14248 424/449 |
| 4,619,652 | A * | 10/1986 | Eckenhoff | A61M 5/14248 604/145 |
| 4,753,651 | A * | 6/1988 | Eckenhoff | A61M 5/14248 424/449 |
| 7,517,440 | B2 | 4/2009 | Anex et al. | |
| 7,803,148 | B2 * | 9/2010 | Lobl | A61M 5/1409 424/422 |
| 2002/0123740 | A1 * | 9/2002 | Flaherty | A61M 5/14248 604/890.1 |
| 2002/0182113 | A1 * | 12/2002 | Shvets | A61M 5/1452 422/505 |
| 2003/0212379 | A1 * | 11/2003 | Bylund | A61B 5/14514 604/504 |
| 2004/0199123 | A1 * | 10/2004 | Nielsen | A61M 5/14 604/180 |
| 2005/0247558 | A1 * | 11/2005 | Anex | A61M 5/14248 204/275.1 |
| 2007/0066939 | A1 * | 3/2007 | Krulevitch | A61M 5/16831 604/152 |
| 2009/0163874 | A1 * | 6/2009 | Krag | A61M 5/14248 604/180 |
| 2010/0185178 | A1 * | 7/2010 | Sharp | A61M 5/002 604/506 |
| 2010/0318032 | A1 * | 12/2010 | Togawa | A61M 5/1413 604/151 |
| 2011/0180464 | A1 * | 7/2011 | Schmitt | B01D 61/08 210/86 |
| 2013/0060233 | A1 * | 3/2013 | O'Connor | A61M 5/158 604/506 |
| 2013/0338592 | A1 * | 12/2013 | Calasso | A61M 5/14232 604/151 |
| 2017/0189609 | A1 * | 7/2017 | Wei | A61M 5/14526 |
| 2018/0021508 | A1 * | 1/2018 | Destefano | A61M 5/158 604/151 |
| 2019/0009020 | A1 * | 1/2019 | Kim | A61M 5/00 |
| 2019/0091408 | A1 * | 3/2019 | Kim | A61M 5/20 |

FOREIGN PATENT DOCUMENTS

| | | |
|---|---|---|
| JP | 2012-115673 | 6/2012 |
| KR | 10-1420360 | 7/2014 |
| KR | 10-2014-0101255 | 8/2014 |
| WO | 2016-130679 | 8/2016 |

\* cited by examiner

LIQUID MEDICINE INJECTION DEVICE

TECHNICAL FIELD

The present invention relates to a liquid medicine injection device attached to a patient's body to inject a liquid medicine such as insulin into the patient's body at an appropriate time.

BACKGROUND ART

In general, a liquid medicine injection device such as an insulin injection device is used to inject a liquid medicine into a patient's body. Such a liquid medicine injection device is used by medical professionals such as a doctor or a nurse, but it is mostly used by an ordinary person such as a patient himself or a caregiver. In case of diabetic patients, particularly diabetic children, it is necessary to inject liquid medicine such as insulin into a human body at regular intervals. Thus, a patch-type liquid medicine injection device that can be used by being attached to a human body for a predetermined period of time has been researched and developed. Such a liquid medicine injection device may be used while being attached as a patch type to the abdomen or waist of a patient for a predetermined period of time.

In order to be attached to a human body, the liquid medicine injection device needs to be excellent wearable sensation, comfortable to use, excellent in durability, and driven with low power. In addition, for daily life of the patient, the liquid medicine injection device requires an excellent waterproofing function, and a product to be sold needs to remain sterile. However, a conventional liquid medicine injection device cannot satisfy such conditions.

DISCLOSURE

Technical Problem

The present invention has been made in an effort to resolve the above-described problems, and provides a liquid medicine injection device that can provide an excellent wearable sensation and can be driven with low power, and thus can be used by being attached to a human body for a sufficiently long period of time.

Another purpose of the present invention is to provide a liquid medicine injection device that can be easily used by a patent or a caregiver rather than by medical professionals.

Another purpose of the present invention is to provide a liquid medicine injection device of which an operation fluid of a driving pump that is driven for injection of a liquid medicine into a human body is completely separated from the liquid medicine, thereby improving reliability of the product.

Another purpose of the present invention is to provide a liquid medicine injection device of which a needle assembly that injects a liquid medicine has a rigid structure, and can accurately inject a liquid medicine according to intention of a patient.

Another purpose of the present invention is to provide a liquid medicine injection device that can be manufactured in a compact manner, thereby reducing manufacturing cost and providing convenience in use of the device.

Another purpose of the present invention is to provide a liquid medicine injection device that can satisfy a condition as a medical tool by maintaining a sterile state before being used by a patient after being released as a product.

Another purpose of the present invention is to provide a liquid medicine injection device that can protect a patient by a fail-safe function when a problem occurs in liquid medicine injection.

Another purpose of the present invention is to provide a liquid medicine injection device that enables a remaining amount of liquid medicine received therein to be easily checked from the outside, thereby providing proper replacement period and preventing unnecessary operation.

Another purpose of the present invention is to provide a liquid medicine injection device that can minimize inconvenience in daily life of a patient, such as showering, even when the device is attached to the patient's body, by maximizing a waterproof function.

Another purpose of the present invention is to provide a liquid medicine injection device that can control an injection time of a liquid medicine, a remaining amount of the liquid medicine, operation of injection of the liquid medicine, and the like, and enables a patient or a user to check and record the injection time of the liquid medicine, the remaining amount of the liquid medicine, and the operation of the injection of the liquid medicine as data in a database to thereby maximize a medical examination effect when medical staff regularly examines the patient.

Technical Solution

In order to achieve such a purpose, the present invention provides a liquid medicine injection device including: a case; a liquid medicine tank that is disposed in the case and where liquid medicine is received; an electro-osmosis pump that is connected with the liquid medicine tank and moves the liquid medicine; a needle assembly that receives the liquid medicine by being connected to the electro-osmosis pump and injects the received liquid medicine into a human body; and an adhesive member combined to the case and attached to the human body.

The electro-osmosis pump preferably includes: a connector provided with a liquid medicine inlet and a liquid medicine outlet; a check valve assembly combined to one side of the connector; and a driver that is connected to the other side of the connector and moves the liquid medicine toward the liquid medicine outlet by applying pressure to the liquid medicine while being separated from the liquid medicine, which passes through the check valve assembly.

The check valve assembly preferably includes: an inflow check valve that is disposed in the liquid medicine inlet to move the liquid medicine in one direction; and a discharge check valve that is disposed in the liquid medicine outlet to discharge the liquid medicine transmitted through the inflow check valve.

The driver preferably includes: a first diaphragm that is combined to the connector and blocks liquid medicine of the check valve assembly; a first pump housing that is combined to the first diaphragm and provided with a space where an operation fluid is received; a first power supply line that is combined to the first pump housing and receives power; a first electrode connected to the first power supply line; a membrane of which one side is combined to the first electrode; a second electrode combined to the other side of the membrane; a second power supply line that supplies power to the second electrode; a second pump housing combined to one side of the second electrode and provided with a space where an operation fluid is received; and a second diaphragm combined to the second pump housing.

The needle assembly preferably includes: a knob; a rotation member that rotates with rotation of the knob and provided with a locking protrusion portion in an internal wall thereof; a moving member that is accommodated in the rotation member and moves in an axial direction or is fixed at a predetermined position by movement of the locking protrusion portion; a needle combined to the moving member; and a spring that is elastically supported between the rotation member and the moving member, and the moving member preferably includes: a first locking groove portion that is supported by the locking groove portion; a straight line guide groove portion that is connected with the first locking groove portion and provided along an axial direction to guide the locking protrusion portion; a slope guide groove portion that is connected with the straight line guide groove portion and provided along a slope direction to guide the locking protrusion portion; and a second locking groove portion that is connected with the slope guide groove portion and supported by the locking groove portion.

The liquid medicine injection device includes a liquid medicine remaining amount checking portion, and the liquid medicine remaining amount checking portion preferably includes: a first electrode plate received in the liquid medicine tank; a second electrode plate that is received in the liquid medicine tank and disposed at distance from the first electrode plate; and a detection sensor that senses capacitance that varies according to a remaining amount of the liquid medicine between the first electrode plate and the second electrode plate and transmits a sensed signal to a controller.

The liquid medicine injection device includes an operation switch, and the operation switch preferably includes: a magnet provided in the piston that is accommodated in the liquid medicine tank; and a magnet detection sensor that senses movement of the magnet and transmits a sensed result to a controller, wherein the controller receives the signal from the magnet detection sensor and supplies power to control the liquid medicine injection device to be in an operable state.

Advantageous Effects

The liquid medicine injection according to the present invention can be manufactured in a compact manner, and can provide excellent wearable sensation by being attached to a human body using an adhesive member and can be driven with low power for a sufficiently long period of time by being attached to a human body.

According to the present invention, when a user can easily use the device since power is automatically supplied to the device and thus the device is changed to an operable state when the injects liquid medicine into the liquid medicine tank, and thus a patient or a caregiver of the patient who is not a medical professional.

According to the the present invention, a compach-structured electro-osmosis pump is adopted and thus liquid medicine injected into a human body and operation fluid of the electro-osmosis pump driven for injection of the liquid medicine into the human body can be completely separated from each other, thereby improving reliability of the product.

According to the present invention, a needle provided in the needle assembly that injects liquid medicine can be inserted into a human body when a user rotates the knob by a predetermined angle, and when the user further rotates the knob, the needle can be separated from the human body so that a presice amount of liquid medicine can be injected into the human body as a patient's intention, and the needle assembly can be formed in a rigid structure, thereby improving the merchantability.

The present invention can be manufactured in a compact manner by applying a very small size electroosmotic pump, thereby reducing manufacturing costs.

According to the present invention, the liquid medicine injection device that can satisfy a condition as a medical tool by maintaining a sterile state before being used by a patient after being released as a product.

According to the present invention, a patient can be protected by a fail-safe function when a problem occurs in liquid medicine injection.

According to the present invention, a remaining amount of liquid medicine received therein can be easily checked from the outside, thereby providing proper replacement period and preventing unnecessary operation.

According to the present invention, inconvenience in daily life of a patient, such as showering, can be minimized even when the device is attached to the patient's body, by maximizing a waterproof function.

According to the present invention, an injection time of a liquid medicine, a remaining amount of the liquid medicine, operation of injection of the liquid medicine, and the like, can be controlled and a patient or a user can check and record the injection time of the liquid medicine, the remaining amount of the liquid medicine, and the operation of the injection of the liquid medicine as data in a database to thereby maximize a medical examination effect when medical staff regularly examines the patient.

MODE FOR INVENTION

Figure 1:
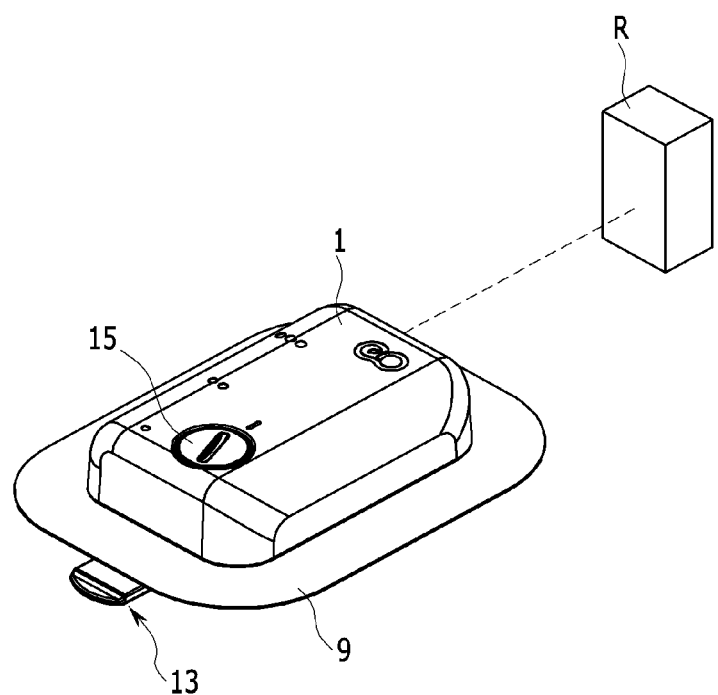
FIG. 1 shows an external appearance of a liquid medicine injection device for description of an exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 2:
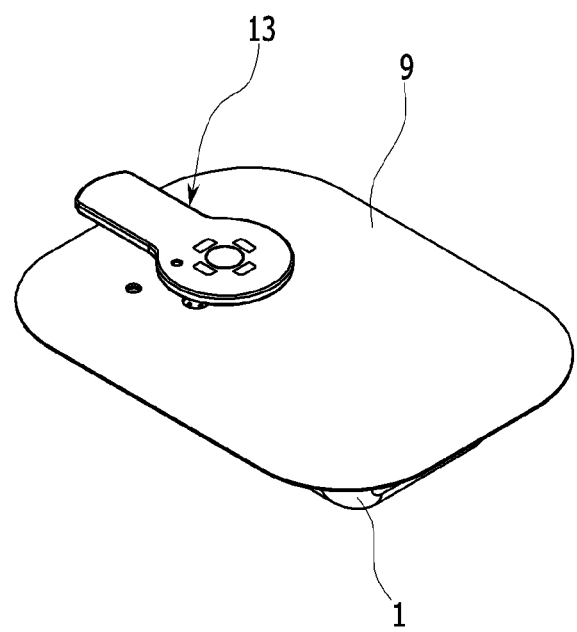
FIG. 2 is a perspective view of a bottom side of FIG. 1.
Figure 3:
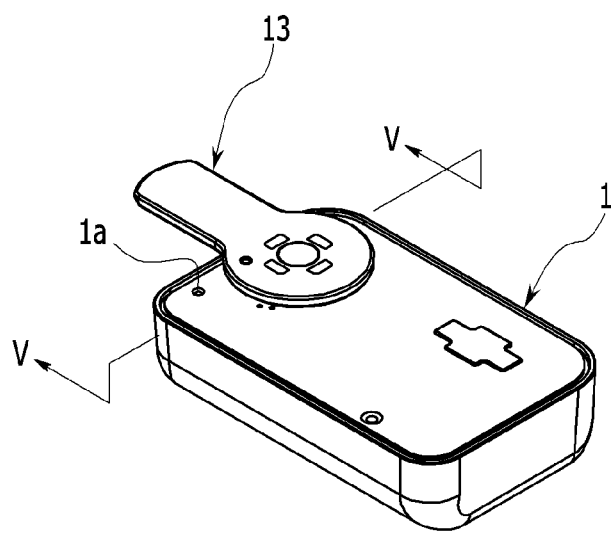
FIG. 3 is a perspective view of main parts of the bottom side of the liquid medicine injection device according to the exemplary embodiment of the present invention.
Figure 4:
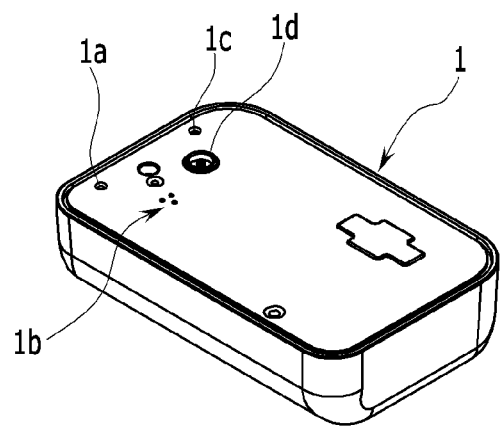
FIG. 4 is a perspective view of a bottom side of a case according to the exemplary embodiment of the present invention.
Figure 5:
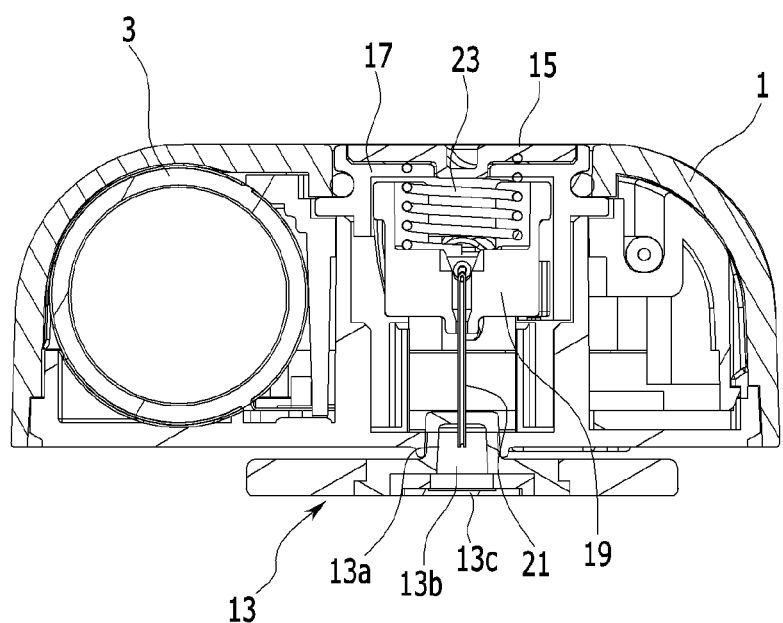
FIG. 5 is a cross-sectional view of FIG. 3, taken along the line V-V.
Figure 6:
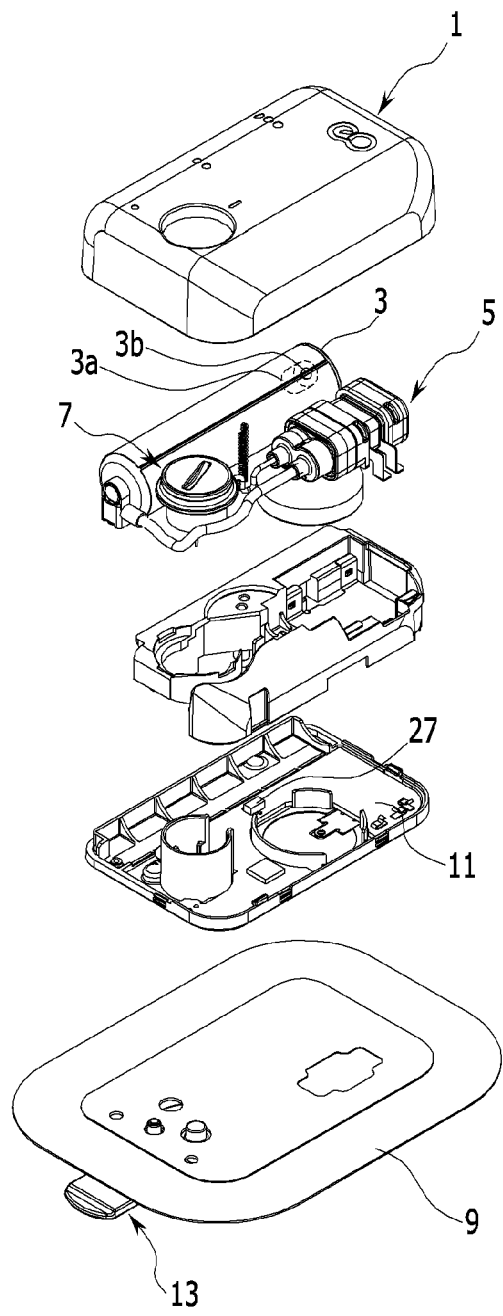
FIG. 6 is an exploded perspective view of FIG. 1.

FIG. 1 is a perspective view of an exemplary embodiment of the present invention, FIG. 2 is a bottom perspective view of a main part of FIG. 1, FIG. 3 is a bottom perspective view of the main part of FIG. 3, FIG. 4 is a bottom perspective view of the main part of FIG. 1, FIG. 5 is a cross-sectional view of FIG. 3, taken along the line V-V, and FIG. 6 is an exploded perspective view of FIG. 1, which illustrates a liquid medicine injection device.

A liquid crystal injection device according to an exemplary embodiment of the present invention includes a case 1, a liquid medicine tank 3, an electro-osmosis pump 5, a needle assembly 7, and an adhesive member 9.

The case 1 may be formed by combining a lower case and an upper case, and in the exemplary embodiment of the present invention, the combination of the lower case and the upper case will be referred to as the case 1.

The adhesive member 9 is bonded to one side of the case 1 to attach the case 1 to a human body. A receiving space is provided in the case 1 such that the liquid medicine tank 3, the electro-osmosis pump 5, and the needle assembly 7 are accommodated therein. In addition, a controller 11 that drives the electro-osmosis pump 5 according to an operation signal may be received in the case 1. In the controller 11, electronically operated chips are disposed in a printed circuit board to receive input signals of sensors to control operation and power supply of the electro-osmosis pump 5. Such a controller 11 may be controlled by a portable communication device such as smart phone where a remote controller or a control application is installed.

In one side of the case 1, a liquid medicine injection hole portion 1a, a sterilized gas circulation hole portion 1b, a reset button portion 1c, and a needle penetration hole portion 1d are provided.

The liquid medicine injection hole portion 1a is connected with the liquid medicine tank 3 to supply a liquid medicine to the liquid medicine tank 3 from the outside by using a syringe and the like.

The sterilized gas circulation hole portion 1b may block introduction of a fluid such as water from the outside, while letting gas such as sterilized gas pass through. A plurality of small holes are disposed in such a sterilized gas circulation hole portion 1b, while penetrating therethrough. In addition, a member such as Tyvek (product name), Gore-Tex (product name), and/or a non-woven fabric, which can block a fluid while transmitting a gas is combined to the inside of the case 1 of the sterilized gas circulation hole portion 1b. Thus, introduction of a fluid such as water into the case 1 can be blocked and gas can freely flow in and out the case 1 in the sterilized gas circulation hole portion 1b.

Such sterilized gas circulation hole portion 1b functions to prevent permeation of a contamination source or moisture, for example, an external virus and the like, into a product when a user uses the product. Thus, according to the present invention, the sterilized gas circulation hole portion 1b is provided to enable sterilization using ethylene oxide gas, and provides user convenience by enabling a user to carry out daily life such as showering and the like even when the liquid medicine injection medicine is attached to the user's body.

A reset bottom portion 1c is connected with the controller 11, and thus when a problem occurs in the liquid medicine injection device, operation of the liquid medicine injection device can be externally stopped by the user. The reset bottom portion 1c provides a fail safe function, and thus it prevents a patient from being supplied with unnecessary liquid medicine.

A needle protection member 13 may be fitted into a needle penetration portion 1d. A needle provided in the needle assembly 7 is fitted into the needle protection member 13, and a certain space may be provided in a portion where the needle is fitted. Liquid medicine is injected into the liquid medicine tank 3 while the needle protection member 13 is embedded in the liquid medicine device, and then the user removes the needle protection member 13 for use. The needle protection member 13 not only protects the needle of the needle assembly 7 during a distribution process of the liquid medicine injection device, but also collects some of liquid medicine flowing through the needle when the liquid medicine is injected into the liquid medicine tank 3 through the liquid medicine injection hole portion 1a and safely processes the collected liquid medicine.

As shown in FIG. 5, the needle protection member 13 can protect the needle by receiving the needle in a space 13b in a liquid medicine leakage prevention container 13a, which is formed of a rubber material. The user removes the needle protection member 13 and attaches the liquid medicine injection device to a human body. When the user removes the needle protection member 13, the needle in a state of being protected by the liquid medicine leakage prevention container 13a can be injected into a human body.

An outer surface of the needle protection member 13 is sealed with a moisture-permeable and waterproof member 13c such as Gore-Tex (trade name) supplied from Gore or Tyvek (trade name) supplied from DuPont, and thus when the liquid medicine injection device is initially primed, leakage of the liquid medicine can be prevented and air can be passed therethrough.

Such a needle protection member 13 is preferably disposed in the outermost side of an adhesive member 9. The needle protection member 13 according to the exemplary embodiment of the present invention can be easily handled by a user and can further improve merchantability of the liquid medicine injection device.

The liquid medicine tank 3 may accommodate the liquid medicine, and is connected to the electro-osmosis pump 5 through a pipe. That is, liquid medicine accommodated in the liquid medicine tank 3 may move to the needle assembly 7 by operation of the electro-osmosis pump 5.

The liquid medicine tank 3 may be substantially formed in the shape of a cylinder, and a piston 3a is provided therein. The piston 3a provided in the liquid medicine tank 3 moves (retracts) by a force applied when the liquid medicine is injected into the liquid medicine tank 3, and can return to its initial position when the liquid medicine passes through the needle. In addition, as shown in FIG. 6, a magnet 3b may be combined to one side of the piston 3a. The magnet 3b is preferably disposed at the opposite side of a portion where the liquid medicine contacts the piston 3a.

Figure 13:
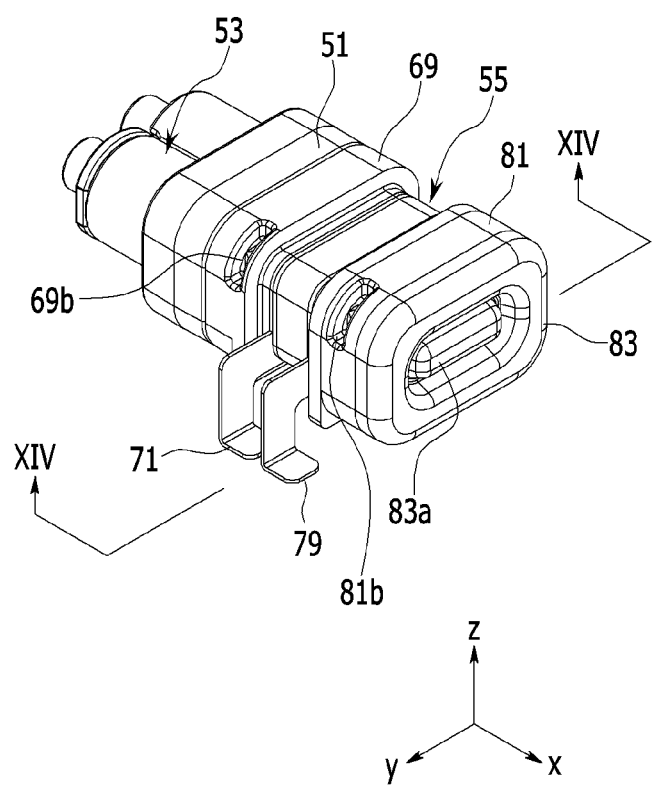
FIG. 13 is a perspective view of an external appearance of an electro-osmosis pump according to the exemplary embodiment of the present invention.
Figure 14:
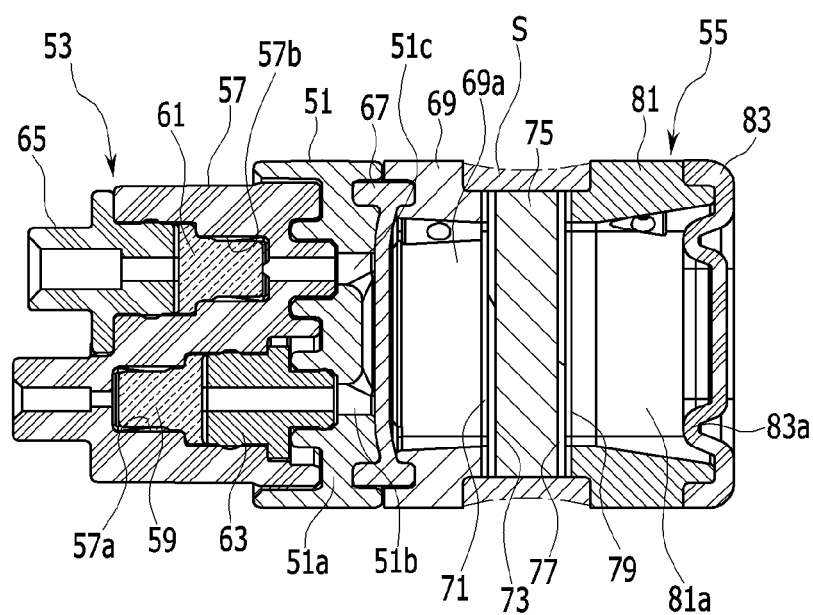
FIG. 14 is a cross-sectional view of FIG. 13, taken along the line XIV-XIV.

As shown in FIG. 13 and FIG. 14, the electro-osmosis pump 5 includes a connector 51, a check valve assembly 53, and a driver 55.

The check valve assembly 53 is combined to one side of the connector 51, and the driver 55 may be combined to the other side thereof. The connector 51 is provided with a barrier rib 51a that partitions the check valve assembly 53 and the driver 55. A liquid medicine inlet 51b and a liquid medicine outlet 51c are provided in the barrier rib 51a.

The liquid medicine inlet 51b and the liquid medicine outlet 51c are disposed at a distance from each other, while penetrating the barrier rib 51a.

Liquid medicine to be put into a human body is put into the liquid medicine inlet 51b, and the liquid medicine outlet 51c may be a path through which the liquid medicine put into the liquid medicine inlet 51b is discharged so as to be put back into the human body.

The check valve assembly 53 may include a valve housing 57, an inflow check valve 59, a discharge check valve 61, a first fixing hole 63, and a second fixing hole 65.

A liquid medicine inflow extension pipeline 57a and a liquid medicine discharge extension pipeline 57b are provided in the valve housing 57. The valve housing 57 may be combined to one side of the connector 51. In addition, the liquid medicine inflow extension pipeline 57a is connected to the liquid medicine inlet 51b, and the liquid medicine discharge extension pipeline 57b is connected to the liquid medicine outlet 51c.

The inflow check valve 59 is disposed in the liquid medicine inflow extension pipeline 57a. The inflow check valve 59 may let liquid medicine injected into a human body pass to the liquid medicine inlet 51b and block movement of the liquid medicine in the reverse direction.

The discharge check valve 61 is disposed in the liquid medicine discharge extension pipeline 57b. The discharge check valve 61 may let the liquid medicine passed through the liquid medicine inlet 51b pass in a direction of injection into the human body, and blocks movement in the reverse direction.

As the inflow check valve 59 and the discharge check valve 61, duckbill valves that are flexible and have a low open-pressure may be used. Fluid transmission efficiency compared to a power consumption amount is increased by the inflow check valve 59 and the discharge check valve 61, thereby enabling long-time operation and improving productivity.

The first fixing hole 63 is fitted into the liquid medicine inflow extension pipeline 57a to fix the inflow check valve 59. The second fixing hole 65 is fitted into the liquid medicine discharge extension pipeline 57b to fix the discharge check valve 61.

In addition, the first fixing hole 63 and the second fixing hole 65 preferably have pipelines through which liquid medicine can pass.

In the exemplary embodiment of the present invention, the inflow check valve 59 and the discharge check valve 61 are combined to the valve housing 57, but this is not restrictive, and the inflow check valve 59 and the discharge check valve 61 may be respectively combined to the liquid medicine inlet 51b and the liquid medicine outlet 51c provided in the connector 51. In this case, the valve housing 57 is integrally formed with the connector 51 so that it can be manufactured with a simpler structure. According to the other exemplary embodiment of the present invention, the number of parts is reduced so that manufacturing cost can be more saved, and the product can be manufactured to be more compact.

The driver 55 is combined to one side of the connector 51. The driver 55 is preferably disposed opposite to a side where the check valve assembly 53 is combined. The driver 55 is preferably disposed apart from the liquid medicine that passes through the check valve assembly 53. The driver 55 applies pressure to the liquid medicine passed through the check valve assembly 53 such that the liquid medicine can pass through the liquid medicine outlet 51c.

The driver 55 may include a first diaphragm 67, a first pump housing 69, a first power supply line 71, a first electrode 73, a membrane 75, a second electrode 77, a second power supply line 79, a second pump housing 81, and a second diaphragm 83.

The first diaphragm 67 is combined to one side of the connector 51. A space is provided between the first diaphragm 67 and the connector 51. That is, the first diaphragm 67 is combined to the connector 51, while maintaining a certain space in the connector 51. Thus, liquid medicine at the check valve assembly 53 maintains a state of being isolated rather than moving toward the driver 55 by the first diaphragm 67.

A plane portion of the first diaphragm 67 can iteratively move in a predetermined section in an axial direction by a pressure generated from the driver 55. A wrinkle portion may be provided in the first diaphragm 67 to allow the plane portion of the first diaphragm 67 to smoothly move along the axial direction (i.e., the x-axis direction in FIG. 1).

The first diaphragm 67 is combined to one side of the first pump housing 69. The first pump housing 69 is provided with a space 69a that penetrates along an axial direction. Thus, one side of the space 69a of the first pump housing 69 may be closed by the first diaphragm 67.

The first electrode 73 is combined to the other side of the first pump housing 69 so that the space 69a formed by the first pump housing 69 may be closed. In addition, the first pump housing 69 may accommodate operation fluid such as water and the like in the space 69a provided therein.

The first pump housing 69 may be provided with a fluid injection hole portion 69b at an external circumference thereof. Such a hole portion 69b may be sealed after the operation fluid is injected into the first pump housing 69. Thus, the operation fluid of the driver 55 may be separated from the liquid medicine at the check valve assembly 53.

The first power supply line 71 may supply power to the first electrode 73. The first power supply line 71 is disposed along an edge of the first pump housing 69, and may be fixed to the first electrode 73 by contacting the same. The first power supply line 71 is preferably disposed between the first pump housing 69 and the first electrode 73. However, according to another exemplary embodiment of the present invention, the first power supply line 71 may supply power to the first electrode 73, and may be disposed between the first electrode 73 and the membrane 75.

The first electrode 73 is formed in the shape of a plate and thus may close the space 69a of the first pump housing 69. That is, the first pump housing 69 may form the space 69a with the first diaphragm 67 and the first electrode 73. In addition, the operation fluid such as water and the like is accommodated in the space 69a of the first pump housing 69.

The membrane 75 may be formed of a porous material through which the operation fluid and ions can move. The membrane 75 is preferably made of an insulator such as a ceramic and the like. When the membrane 75 is formed of an insulator, an electro-chemical reaction material used in the first electrode 73 and the second electrode 77 is consumed or desorbed due to long-term driving of the electro-osmosis pump and thus the porous membrane 75 is exposed. However, in this case, even when conventional carbon paper or carbon cloth is used, a side reaction such as electrolysis of water, which occurs due to exposure to carbon paper or carbon cloth, does not occur. Thus, unnecessary power consumption due to a side reaction can be prevented. Therefore, according to the present invention, a safe driving characteristic can be provided and durability can be improved.

The membrane 75 may be used by processing a flexible non-conductive material such as a polymer resin, rubber, urethane, or a plastic film into a thin film form.

The second electrode 77 is disposed at the other side of the membrane 75. That is, the membrane 75 is preferably disposed between the first electrode 73 and the second electrode 77. The second power supply line 79 may supply external power to the second electrode 77. The second power supply line 79 may be combined to an edge of the second pump housing 81. However, the second power supply line 79 may have any alignment structure as long as it has a structure for supplying power to the second electrode 77.

The shape of the second pump housing 81 is the same as or similar to the shape of the first pump housing 69. Another space 81a that penetrates the second pump housing 81 along an axial direction is provided in the second pump housing 81. As in the first pump housing 69, a hole portion 81b that penetrates the space 81a may be provided in the second pump housing 81. The hole portion 81b of the second pump housing 81 may be sealed by a sealant or filled by welding and the like after operation fluid is injected therein.

The second diaphragm 83 is combined to one side of the second pump housing 81 and thus may close the space 81a provided in the second pump housing 81.

That is, the second pump housing 81 may close the space 81a by using the second electrode 57, which is formed in the shape of a plate, and the second diaphragm 83.

A wrinkle portion 83a may be formed in a plane of the second diaphragm 83. The wrinkle portion 83a formed in the second diaphragm 83 may be formed of protrusions and depressions that protrude in the axial direction with reference to a cross-section. The wrinkle portion 83a of the second diaphragm 83 enhances performance of pumping by sufficiently moving the plane portion of the second diaphragm 83 along the axial direction.

In the exemplary embodiment of the present invention, the wrinkle portion 83a is formed in the second diaphragm 83, but depending on exemplary embodiments, a wrinkle portion may be also formed in the first diaphragm 67. In addition, a wrinkle portion that can be formed in the first diaphragm 67 or the second diaphragm 83 maximizes deformation of the first diaphragm 67 and the second diaphragm 83 with small energy, thereby reducing energy consumption. That is, the driver 55 can be driven for a long period of time with a small external power source.

As shown in FIG. 14, the above-described first pump housing 69, the first power supply line 71, the first electrode 73, the membrane 75, the second electrode 77, the second power supply line 79, and the second pump housing 81 may be air-tightly sealed from the outside by an encapsulant S. That is, the first power supply line 71, the first electrode 73, the membrane 75, the second electrode 77, and the second power supply line 79 are formed relatively smaller than the first pump housing 69 and the second pump housing 81 in size, and thus the encapsulant S may be disposed in a circumferential portion (i.e., a portion exposed to the outside and a portion that forms a groove or a space with reference to a cross-section) between the first pump housing 69 and the second pump housing 81 while the first power supply line 71, the first electrode 73, the membrane 75, the second electrode 77, and the second power supply line 79 are in an assembled state. Such an encapsulant S may form an encapsulation layer that maintains air-tight encapsulation from the outside.

As the encapsulant, an adhesive such as a hot melt adhesive, an epoxy adhesive, a polyurethane adhesive, or a cyanoacrylate adhesive may be used. However, the encapsulant is not limited to such examples, and any material that is rigidly cured to prevent leakage of operation fluid and prevent deformation of an external appearance of a configuration element is applicable.

The needle assembly 7 is connected with the electro-osmosis pump 5, and receives liquid medicine and injects the received liquid medicine into a human body.

Figure 7:
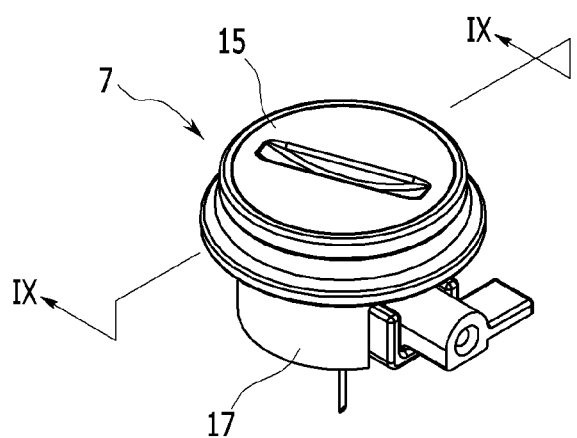
FIG. 7 is a perspective view of a needle assembly for description of the exemplary embodiment of the present invention.
Figure 8:
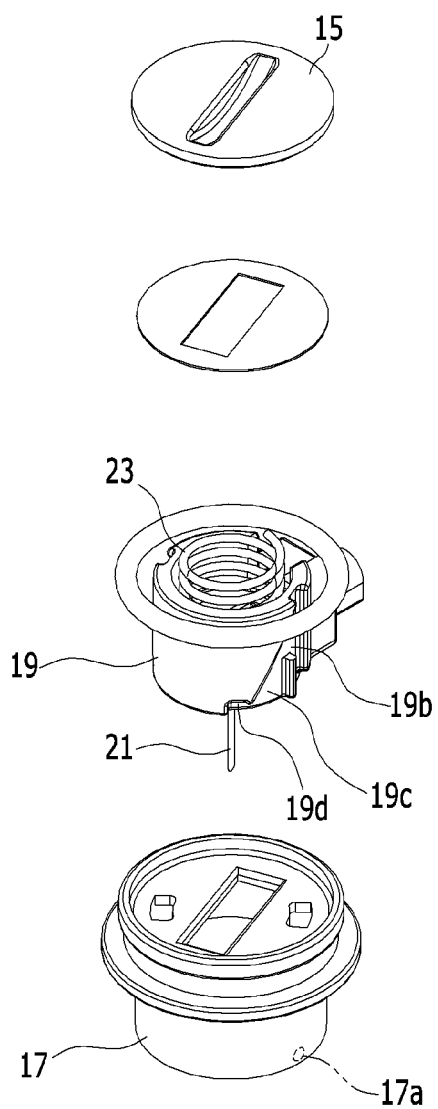
FIG. 8 is an exploded perspective view of FIG. 7.
Figure 9:
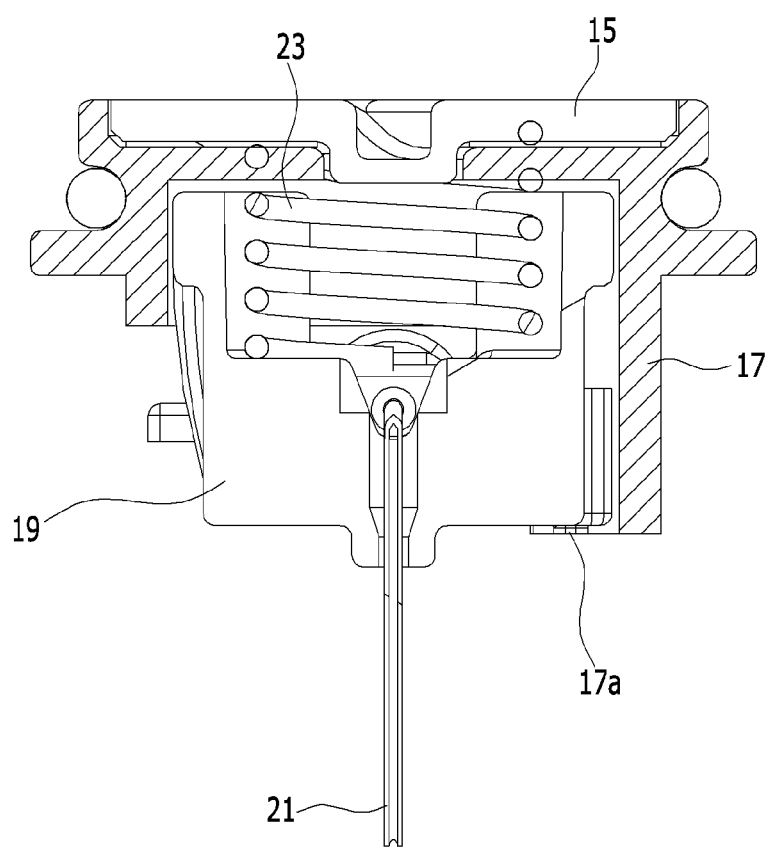
FIG. 9 is a cross-sectional view of FIG. 7, taken along the line IX-IX.

As shown in FIG. 7 to FIG. 9, the needle assembly 7 includes a knob 15, a rotation member 17, a moving member 19, a needle 21, and a spring 23.

A long groove is formed on a top surface of the knob 15, and thus a user can rotate the knob by using a tool such as a coin, a driver, and the like.

The rotation member 17 is combined with the knob 15 and thus may rotate together with the knob 15. The rotation member 17 may be formed in the shape of an approximate cylinder, and a space may be formed therein. In addition, the rotation member 17 includes a locking protrusion portion 17a protruding from one internal wall thereof.

The moving member 19 is inserted into the internal space of the rotation member 17. The moving member 19 may move a certain distance in the axial direction with respect to the rotation member 17. That is, with reference to FIG. 9, the moving member 19 may relatively vertically move with respect to the rotation member 17. Such a moving member 19 may move axially or may be fixed at a predetermined position with respect to the movement of the locking protrusion portion 17a of the rotation member 17.

The moving member 19 may include a first locking groove portion 19a, a straight line guide groove portion 19b, a slope guide groove portion 19c, and a second locking groove portion 19d, which are formed at an exterior circumferential surface of the moving member 19.

The first locking groove portion 19a may be formed at one side of the exterior circumferential surface of the moving member 19. The locking protrusion portion 17a of the rotation member 17 is inserted into the first locking groove portion 19a such that the moving member 19 can be fixed at a predetermined position. When the first locking groove portion 19a of the moving member 19 and the locking protrusion portion 17a of the rotation member 17 are engaged with each other, the moving member 19 may be accommodated in the rotation member 17. That is, with reference to FIG. 9, it is preferable that the first locking groove portion 19a is disposed at a lower portion of the moving member 19 and the locking protrusion portion 17a is disposed at a lower portion of the rotation member 17a.

The straight line guide groove portion 19b is connected with the first locking groove portion 19a and disposed at an exterior circumferential surface in parallel with a vertical direction with reference to FIG. 9. The straight line guide groove portion 19b is preferably formed in the shape of a straight-lined groove.

Figure 10:
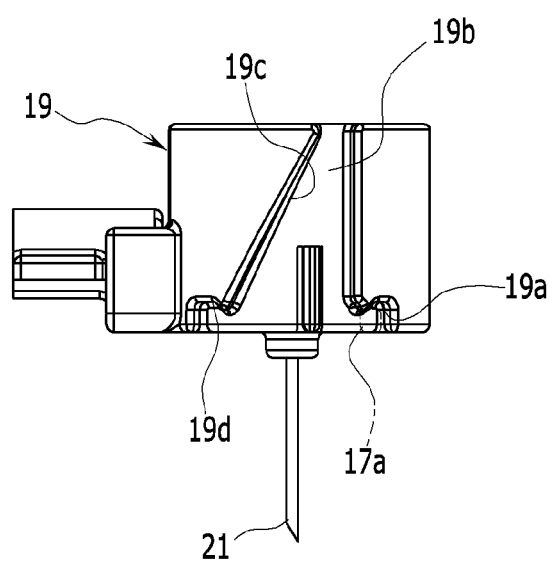
FIG. 10 to FIG. 12 are provided for description of an operation process of the needle assembly according to the exemplary embodiment of the present invention.
Figure 11:
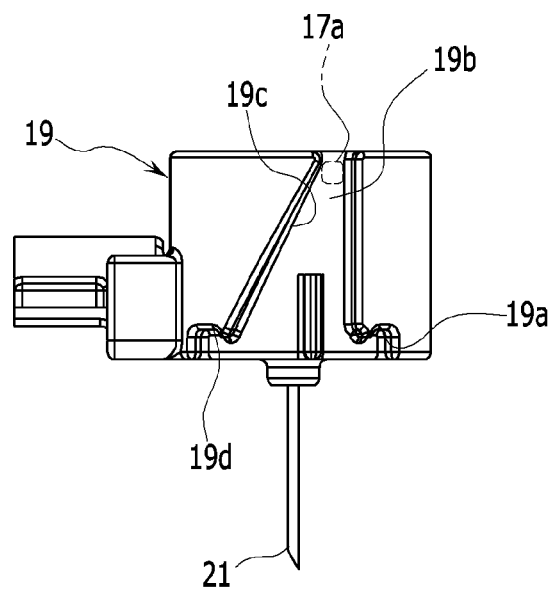
Figure 12:
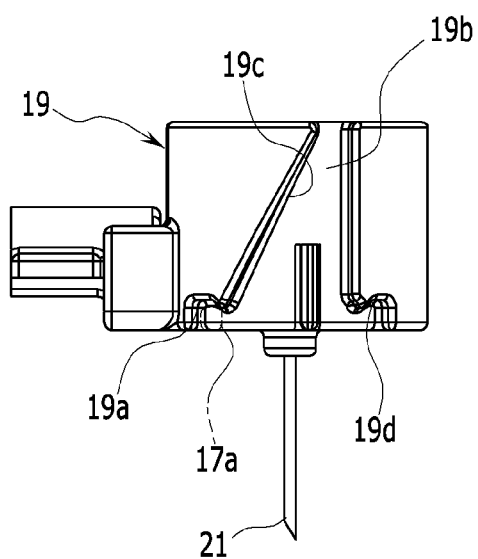

The straight line guide groove portion 19b may guide the locking groove portion 17a, and may extend to an upper portion of the moving member 19 (refer to FIG. 10).

The slope guide groove portion 19c is connected with the straight line guide groove portion 19b and preferably inclined in the form of a helicoid at the exterior circumferential surface of the moving member 19. The slope guide groove portion 19c may be disposed in a downwardly inclined direction at the exterior circumferential surface of the moving member 19.

The second locking groove portion 19d extends to the slope guide groove portion 19c and thus may be disposed at the exterior circumferential surface of the moving member 19. The locking protrusion portion 17a is inserted into the second locking groove portion 19d and thus the moving member 19 may maintain a state of being inserted into the rotation member 17.

The needle 21 is combined to the moving member 19 and is connected thereto to receive liquid medicine transmitted through the electro-osmosis pump 5. The needle 21 may inject the received liquid medicine into a human body.

When the locking groove portion 17a of the rotation member 17 is supported by the first locking groove portion 19a of the moving member 19, the needle 21 maintains a state of being accommodated in the case 1. When the locking groove portion 17a of the rotation member 17 is disposed at the upper portion of the straight line guide groove portion 19b, the needle 21 is in a state of being protruded from the case 1 so as to be inserted into a human body.

In addition, when the locking groove portion 17a of the rotation member 17 moves along the slope guide groove portion 19c and then is fixed to the second locking groove portion 19d, the needle 21 is in a state of being accommodated back into the case 1.

The spring 23 is disposed between the moving member 19 and the rotation member 17. The spring 23 may be formed of a compressive coil spring, and one side of the spring 23 is fixed to the rotation member 17 and the other side thereof is fixed to the moving member 19 or elastically supports the moving member 19.

Figure 15:
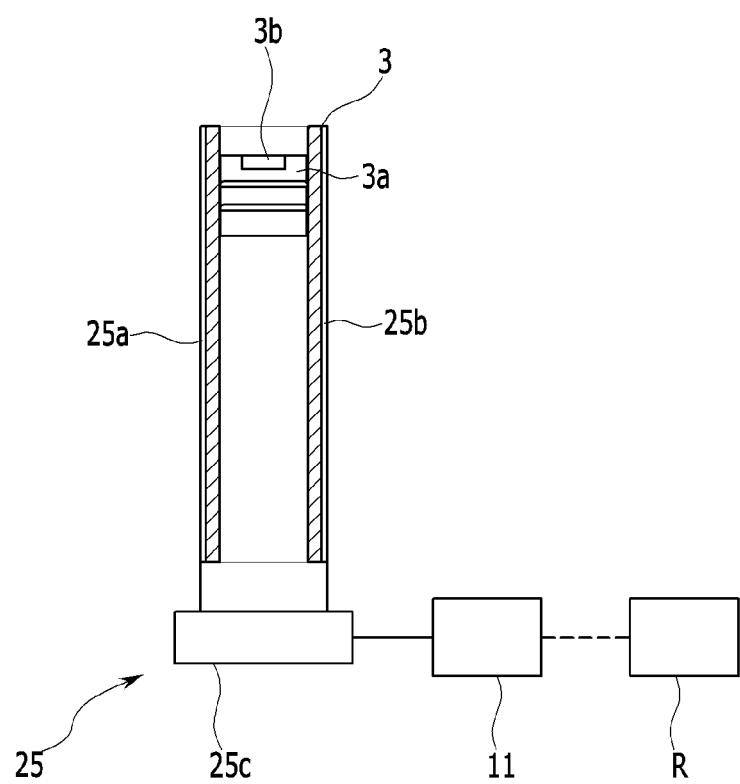
FIG. 15 is provided for description of an example of determination of a liquid medicine remaining amount in a liquid medicine tank according to the exemplary embodiment of the present invention.

As shown in FIG. 15, the liquid medicine injection device according to the exemplary embodiment of the present invention may include a liquid medicine remaining amount checking portion 25. The liquid medicine remaining amount checking portion 25 includes a first electrode plate 25a and a second electrode plate 25, which are disposed apart from each other in the liquid medicine tank 3. The first electrode plate 25a and the second electrode plate 25b are preferably disposed with the liquid medicine therebetween.

In addition, the first electrode plate 25a and the second electrode plate 25b are connected with a detection sensor 25c. The detection sensor 25c senses capacitance that varies depending on the amount of liquid medicine between the first electrode plate 25a and the second electrode plate 25b, and transmits the sensed value to the controller 11.

The liquid medicine remaining amount checking portion 25 of the exemplary embodiment of the present invention is not limited to the above-described liquid medicine remaining amount checking portion 25, and a linear encoder and the like may be used to detect the amount of liquid medicine depending on position variation of the piston 3a as an another exemplary embodiment of the present invention.

Meanwhile, the liquid medicine injection device according to the exemplary embodiment of the present invention may include an operation switch 27. The operation switch 27 controls the controller 11 to be in an operation state by a signal of the operation switch 27 while maintaining a non-operation state in the state before use of the product. A magnetic switch or a magnetic sensor is disposed on a printed circuit board, and movement of the magnet 3b provided in the piston 3a can be sensed.

Initial movement of the magnet 3b implies supply of liquid medicine into the liquid medicine tank 3.

Thus, when the magnet 3b moves as the piston 3a moves, the operation switch 27 senses the movement of the magnet 3b and transmits a sense signal to the controller 11 or supplies power to the liquid medicine injection device to controls the liquid medicine injection device to be in an operable state. When the operation switch 27 senses movement of the magnet 3b and transmits a sense signal to the controller 11, the controller 11 controls the liquid medicine injection device to be in an operable state.

An operation process of the above-described exemplary embodiment will now be described.

First, a user injects liquid medicine to the liquid medicine injection hole portion 1 provided in the case 1 of the liquid medicine injection device in a state as shown in FIG. 1 and FIG. 2 by using an additional syringe and the like. Then, the liquid medicine supplied through the liquid medicine injection hole portion 1a is filled in the liquid medicine tank 3.

In this case, the piston 3a of the liquid medicine tank 3 moves by a supply pressure of the liquid medicine injected into the liquid medicine tank 3. Then, the piston 3a moves and the magnet 3 combined to the piston 3a also moves.

The operation switch 27 senses movement of the magnet 3b and supplies power to the liquid medicine injection device by a sense signal to control the liquid medicine injection device to be in an operable state. Meanwhile, when the operation switch 27 transmits a sense signal with respect to the movement of the magnet 3b, the controller 11 supplies power to the liquid medicine injection device such that the liquid medicine injection device is controlled to be in an operable state.

In this case, some of the liquid medicine may be leaked through the needle 21, and the leaked liquid medicine is temporarily stored in a space provided in the needle protection member 13. Then, the liquid medicine can be prevented from flowing to the outside of the case 1 during injection into the liquid medicine tank 3 for convenience in use of the device, thereby improving merchantability.

In addition, the user attaches the liquid medicine injection device to a human body by using the adhesive member 9.

Next, a process for the user to inject the needle 21 into the human body will be described.

First, the moving member 19 of the needle assembly 7 is in a state of being accommodated in the rotation member 17. This implies that the locking protrusion portion 17a of the rotation member 17 is in a state of being supported by the first locking groove portion 19a of the moving member 19.

The user rotates the knob 15 formed in the needle assembly 7 of the liquid medicine injection device in a predetermined direction. The rotation member 17 rotates as the knob 15 rotates and thus the locking protrusion portion 17a of the rotation member 17 is separated from the first locking groove portion 19a of the moving member 19 and moves along the straight line guide groove portion 19b of the moving moving member 19. Then, the moving member 19 straightly moves along an axial direction with respect to the rotation member 17 by an elastic force of the spring 23.

Subsequently, the needle 21 provided in the moving member 19 enters into the human body. The needle 21 is inserted into the human body as deep as about 3 mm to about 10 mm and thus pain can be hardly felt.

In addition, when a signal for injection of liquid medicine into a human body is received at the controller 11 through a remote controller or a mobile communication device, the controller 11 drives the electro-osmosis pump 5. A process for operation of the electro-osmosis pump 5 will now be described in detail.

First, power is supplied such that the first power supply line 71 and the second power supply line 79 have different polarities, and a voltage difference occurs between the first electrode 73 and the second electrode 77. Due to such a voltage difference, positive ions are generated as a result of an electrode reaction in an anode. The positive ions generated from the above-stated reaction move to a cathode and pass through the membrane 25 while pulling the operation fluid together such that a pressure (a pumping force) is generated.

That is, such an electrochemical reaction enables ions and the operation fluid to move to the space 69a of the first pump housing 69 or the space 81a of the second pump housing 81 by passing through the membrane 75.

When the polarity of power of the first electrode 73 and the polarity of power of the second electrode 77 are alternately supplied through the first power supply line 71 and the second power supply line 79, the operation fluid can be iteratively moved to the space 69a of the first pump housing 69 and the space 81a of the second pump housing 81 by the above-described electrochemical reaction.

That is, when an electrode which functions as an anode is changed to serve as a cathode due to alternation of the voltage polarity, an electro-chemical reactant consumed when the electrode is used as an anode can be recovered when the electrode is used as a cathode, and vice versa. Accordingly, the electro-osmosis pump can be continuously driven.

Then, the first diaphragm 67 and the second diaphragm 83 are deformed and a pressure is generated. Such a pressure is applied to a space between the connector 51 and the first diaphragm 67.

Then, the liquid medicine is introduced into the liquid medicine inlet 51b through the liquid medicine inflow extension pipeline 57a by the pressure. The introduced liquid medicine may be injected into a human body while being discharged along the liquid medicine outlet 51c and the liquid medicine discharge extension pipeline 57b.

In this case, the inflow check valve 59 and the discharge check valve 61 allow the liquid medicine to move along only one direction. Thus, the electro-osmosis pump according to the exemplary embodiment of the present invention can safely inject liquid medicine into a human body while using low power.

In particular, since the operation fluid of the driver 55 and the liquid medicine are separated from each other, the electro-osmosis pump 5 of the exemplary embodiment of the present invention can prevent an active component included in the liquid medicine from being spoiled due to an electrochemical reaction.

In addition, according to the present invention, a component included in the operation fluid of the driver 55 can be prevented from being transmitted to the liquid medicine such that a wider range of liquid medicine or operation fluid is applicable.

In addition, according to the present invention, a check valve of which an opening pressure is very low is used so that a reaction speed of the check valve is very fast, and accordingly, the pump can be driven with low power and high efficiency as a whole.

Due to such an operation of the electro-osmosis pump 5, liquid medicine in the liquid medicine tank 3 is transmitted to the needle assembly 7 through the electro-osmosis pump 5. The liquid medicine transmitted to the needle assembly 7 is injected into a human body through the needle 21.

As described, injection of liquid medicine such as insulin and the like into a human body can be periodically and iteratively carried out. That is, an injection amount and an injection time of the liquid medicine are set by using a remote controller or a portable communication device to inject a proper amount of liquid medicine into the human body at a proper time.

When the liquid medicine is injected into the human body through the needle 21, the amount of liquid medicine in the liquid medicine tank 3 is reduced and the piston 3 may move toward its original position corresponding to the reduced amount of the liquid medicine.

When the amount of liquid medicine is changed, the detection sensor 25c senses capacitance in the first electrode plate 25a and the second electrode plate 25b, and transmits a sensed signal value to the controller 11. Then, the controller 11 transmits the received data to a remote controller or a portable communication device such that a user can easily check a residual amount of the liquid medicine from the outside. In addition, the remote controller or the portable communication device records a liquid medicine administration period and the dose of liquid medicine, and the record may be utilized as data when medical staff examines a patient in regular medical examination.

In addition, according to the exemplary embodiment of the present invention, a residual amount of liquid medicine in the liquid medicine tank 3 can be determined by the detection sensor 25c.

When a user wants to detach the liquid medicine injection device from a human body or wants to separate the needle 21 from the human body, the user needs to rotate the knob 15 in the same direction as the above-described rotation direction. Then, the moving member 19 also rotates in the same direction as the rotation direction of the knob 15. Subsequently, the locking groove portion 17a of the rotation member 17 moves along the slope guide groove portion 19c in the straight line guide groove portion 19b and is then supported by the second locking groove portion 19d.

Through such an operation, the moving member 19 maintains a state of being accommodated in the rotation member 17 while overcoming the elastic force of the spring 23. When the moving member 19 is accommodated in the rotation member 17, the needle 21 is also separated from the human body and is thus accommodated in the case 1.

According to such an exemplary embodiment of the present invention, the user can be prevented from being stuck by the needle 21 even after using the liquid medicine injection device, thereby preventing a safety accident.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

The invention claimed is:

1. A liquid medicine injection device comprising:
a case;
a liquid medicine tank that is disposed in the case and where liquid medicine is received;
an electro-osmosis pump that is connected with the liquid medicine tank and moves the liquid medicine;
a needle assembly that receives the liquid medicine by being connected to the electro-osmosis pump and injects the received liquid medicine into a human body; and
an adhesive member combined to the case and for attaching to a human body,
wherein the needle assembly comprises:

a knob;

a rotation member that rotates with rotation of the knob and provided with a locking protrusion portion in an internal wall thereof;

a moving member that is accommodated in the rotation member and moves in an axial direction or is fixed at a predetermined position by movement of the locking protrusion portion;

a needle combined to the moving member; and a spring that is elastically supported between the rotation member and the moving member, and the moving member comprises:

a first locking groove portion that is supported by the locking groove portion;

a straight line guide groove portion that is connected with the first locking groove portion and provided along an axial direction to guide the locking protrusion portion;

a slope guide groove portion that is connected with the straight line guide groove portion and provided along a slope direction to guide the locking protrusion portion; and a second locking groove portion that is connected with the slope guide groove portion and supported by the locking groove portion.

2. The liquid medicine injection device of claim 1, wherein the electro-osmosis pump comprises:

a connector provided with a liquid medicine inlet and a liquid medicine outlet;

a check valve assembly combined to one side of the connector; and a driver that is connected to the other side of the connector and moves the liquid medicine toward the liquid medicine outlet by applying pressure to the liquid medicine while being separated from the liquid medicine, which passes through the check valve assembly.

3. The liquid medicine injection device of claim 2, wherein the check valve assembly comprises:

an inflow check valve that is disposed in the liquid medicine inlet to move the liquid medicine in one direction; and an discharge check valve that is disposed in the liquid medicine outlet to discharge the liquid medicine delivered through the inflow check valve.

4. The liquid medicine injection device of claim 2, wherein the driver comprises:

a first diaphragm that is combined to the connector and blocks liquid medicine of the check valve assembly;

a first pump housing that is combined to the first diaphragm and provided with a first space where an operation fluid is received;

a first power supply line that is combined to the first pump housing and receives power;

a first electrode connected to the first power supply line;

a membrane of which one side is combined to the first electrode;

a second electrode combined to the other side of the membrane;

a second power supply line that supplies power to the second electrode;

a second pump housing combined to one side of the second electrode and provided with a second space where the operation fluid is received; and a second diaphragm combined to the second pump housing.

5. The liquid medicine injection device of claim 1, wherein the liquid medicine injection device comprises a liquid medicine remaining amount checking portion, and the liquid medicine remaining amount checking portion comprises:

a first electrode plate received in the liquid medicine tank;

a second electrode plate that is received in the liquid medicine tank and disposed at distance from the first electrode plate; and a detection sensor that senses capacitance that varies according to a remaining amount of the liquid medicine between the first electrode plate and the second electrode plate and transmits a sensed signal to a controller.

6. The liquid medicine injection device of claim 1, wherein the liquid medicine injection device comprises an operation switch, and the operation switch comprises:

a magnet provided in the piston that is accommodated in the liquid medicine tank; and a magnet detection sensor that senses movement of the magnet and transmits a sensed result to a controller, wherein the controller receives the signal from the magnet detection sensor and supplies power to control the liquid medicine injection device to be in an operable state.

* * * * *